(12) United States Patent
Wohltjen

(10) Patent No.: US 7,484,399 B2
(45) Date of Patent: Feb. 3, 2009

(54) SYSTEM, APPARATUS AND METHOD FOR DISPENSING CHEMICAL VAPOR

(75) Inventor: Henry Wohltjen, Bowling Green, KY (US)

(73) Assignee: Microsensor Systems, Inc., Bowling Green, KY (US)

( * ) Notice: Subject to any disclaimer, the term of this patent is extended or adjusted under 35 U.S.C. 154(b) by 334 days.

(21) Appl. No.: 11/321,032

(22) Filed: Dec. 29, 2005

(65) Prior Publication Data

US 2007/0151319 A1 Jul. 5, 2007

(51) Int. Cl.
*G01N 21/001* (2006.01)
(52) U.S. Cl. ...................................... 73/1.03
(58) Field of Classification Search ................ None
See application file for complete search history.

(56) References Cited

U.S. PATENT DOCUMENTS

| | | | | |
|---|---|---|---|---|
| 3,776,023 | A | * | 12/1973 | Budd et al. ............... 73/1.04 |
| 3,824,836 | A | * | 7/1974 | Lyshkow .................. 73/1.04 |
| 4,351,802 | A | | 9/1982 | Baylis et al. |
| 4,391,781 | A | | 7/1983 | Van Lit |
| 5,363,707 | A | | 11/1994 | Augenblick et al. |
| 5,457,983 | A | * | 10/1995 | Sauvageau et al. ......... 73/1.03 |
| 5,693,538 | A | | 12/1997 | Capuano et al. |
| 5,792,423 | A | | 8/1998 | Markelov |
| 6,234,001 | B1 | * | 5/2001 | Sorensen et al. ........... 73/1.04 |
| 6,286,375 | B1 | | 9/2001 | Ward |
| 6,365,107 | B1 | | 4/2002 | Markelov et al. |
| 6,395,560 | B1 | | 5/2002 | Markelov |
| 2004/0040841 | A1 | | 3/2004 | Gonzalez-Martin et al. |
| 2004/0216508 | A1 | * | 11/2004 | Hirsch et al. .............. 73/1.04 |

\* cited by examiner

*Primary Examiner*—Robert R Raevis
(74) *Attorney, Agent, or Firm*—Kramer Levin Naftalis & Frankel LLP

(57) ABSTRACT

This invention relates to a system for testing the operation of a detection instrument, which comprises a first enclosure having at least two ports and containing a fluid comprising a substance detectable in gas form by the instrument, said fluid being present in part as a vapor phase and in part as a liquid phase in equilibrium with one another, said first enclosure being interconnected with the instrument such that the fluid contained in the first enclosure can be dispensed to the instrument via at least one port of said first enclosure; a second enclosure having at least one port and containing either the same or a different fluid in gas form as compared with the first enclosure, said second enclosure being adapted for selective dispensing of a known or ascertainable mass of the fluid contained therein via at least one port thereof, and being interconnected with the first enclosure such that said mass can be introduced into the volume within said first enclosure through at least one port thereof, thereby to displace a correlative mass of the vapor phase fluid contained in the first enclosure causing said correlative mass to be dispensed to said instrument; and a valve in communicating relationship with said first enclosure and positioned such that, when the first enclosure is interconnected with said instrument, the valve is interposed between the interconnected first enclosure and instrument, which valve is capable of selectively permitting flow to said instrument of said vapor phase fluid dispensed from the first enclosure upon being displaced by said introduction of fluid from the second enclosure; the invention also relates to apparatus for implementing and a method involving same.

21 Claims, 2 Drawing Sheets

SYSTEM, APPARATUS AND METHOD FOR DISPENSING CHEMICAL VAPOR

FIELD OF THE INVENTION

The invention relates to technology for verifying the proper operation of a detection instrument, through release of a known or ascertainable volume of a vapor.

BACKGROUND OF THE INVENTION

Instruments for the detection (including quantitative detection or monitoring) of gaseous chemical species require periodic checking with known reference gas samples to verify their correct operation. Various ways of providing a suitable reference gas sample for calibration purposes are known. These methods include the use of pre-mixed compressed gas standards, calibrated permeation tubes, diffusion tubes, and diluted vapor bubblers.

While some of these alternatives are capable of very high precision and accuracy, known calibration technology tends to be costly, entails inconvenient operations, or requires cumbersome supporting hardware (for example, ovens, pumps, and flowmeters), and is thus impractical for a handheld, low maintenance, or low cost instrument.

A vapor is the volatile, gaseous fraction of a chemical species that exists as a liquid at room temperature and ambient pressure. A very simple and attractive way to generate a vapor is to put the liquid chemical into a partially filled, closed container and allow its headspace to reach equilibrium. At equilibrium, the concentration of the headspace vapor will be dependent on the temperature and pressure of the container and the composition of its contents. The vapor activity of a chemical is defined as the ratio of the partial pressure of the vapor divided by the saturated pressure of the chemical at a given temperature. Therefore, the activity of the vapor at equilibrium with its liquid state in a closed container will have a numerical value equal to one at any given temperature. This means the saturated headspace vapor concentration is a quantitatively reproducible value at a known temperature and pressure.

A difficulty associated with using saturated headspace vapor for the testing and calibration of most chemical detection instruments is that the headspace vapor is usually much too concentrated. In addition, the removal of a large vapor sample from a closed container will result in a severe departures from equilibrium conditions unless the ratio of the volume of the container to the volume of headspace vapor removed is relatively large. Consequently, most instruments require a vapor reservoir of substantial volume to provide a reproducible vapor sample suitable for analysis.

If one could remove a reproducible, small volume from the saturated vapor headspace, then near-equilibrium conditions could be maintained, and a small mass of vapor, appropriate for the sensitivity of the instrument to be calibrated, could be delivered. The problem is to devise a method whereby a small, reproducible volume of vapor can be dispensed from the reservoir containing the saturated headspace vapor.

The most common method involves the use of a microliter syringe. In this manual method, the user inserts a small needle through a rubber septum seal to the vapor container and removes a small aliquot of the headspace vapor. While effective, this method is not well suited for automated operation unless very large and expensive auto-injector robotic systems are employed. See U.S. Pat. No. 5,792,423 (Markelov).

Other methods rely upon the use of stripper gas (also referred to as a "purge" or "carrier" gas), such as nitrogen, to "sweep" a sample of the headspace vapor to a dispersal site, usually a measurement instrument. For instance, see U.S. Pat. No. 5,363,707 (Augenblick et al.), U.S. Pat. No. 6,365,107 (Markelov et al.), U.S. Pat. No. 6,395,560 (Markelov), or U.S. Application Publication No. US 2004/0040841 (Gonzalez-Martin et al.). Another method involves allowing a heated liquid to enter the sample vessel and displace the headspace vapor. See U.S. Pat. No. 6,286,375 (Ward).

Because of the drawbacks attendant upon the above-mentioned approaches, provision of a technology which permits effective testing of a detection instrument while ameliorating such drawbacks would be a significant advance.

OBJECTS OF THE INVENTION

It is an object of the invention to provide a system, apparatus and method for generating small amounts of vapor from chemical species that are liquids or low volatility solids at normal operating conditions.

It is another object of the invention to provide a system, apparatus and method for generating small amounts of vapor suitable for the calibration of high sensitivity detection instruments.

It is yet another object of the invention to provide a system for generating small amount of vapors that is compact and suitable for incorporation into a detection instrument, as well as apparatus for implementing and a method involving same.

It is a further object of the invention to provide a system for generating small amounts of vapor that has an extended operating life and requires minimal maintenance, as well as apparatus for implementing and a method involving same.

SUMMARY OF THE INVENTION

In one aspect, the invention is a system for testing the operation of a detection instrument, which comprises a first enclosure having at least two ports and containing a fluid comprising a substance detectable in gas form by the instrument, said fluid being present in part as a vapor phase and in part as a liquid phase in equilibrium with one another, said first enclosure being interconnected with the instrument such that the fluid contained in the first enclosure can be dispensed to the instrument via at least one port of said first enclosure; a second enclosure having at least one port and containing either the same or a different fluid in gas form as compared with the first enclosure, said second enclosure being adapted for selective dispensing of a known or ascertainable mass of the fluid contained therein via at least one port thereof, and being interconnected with the first enclosure such that said mass can be introduced into the volume within said first enclosure through at least one port thereof, thereby to displace a correlative mass of the vapor phase fluid contained in the first enclosure causing said correlative mass to be dispensed to said instrument; and a valve in communicating relationship with said first enclosure and positioned such that, when the first enclosure is interconnected with said instrument, the valve is interposed between the interconnected first enclosure and instrument, which valve is capable of selectively permitting flow to said instrument of said vapor phase fluid dispensed from the first enclosure upon being displaced by said introduction of fluid from the second enclosure.

In another aspect, the invention is an apparatus for dispensing a known or ascertainable mass of a fluid in gas form to a detection instrument, comprising: a first enclosure adapted for interconnection with the instrument and capable of containing said fluid when present in part as a vapor phase and in part as a liquid phase in equilibrium with one another; interconnected with the first enclosure, a second enclosure capable of containing either the same or a different fluid in gas form as compared with the first enclosure, said second enclosure being adapted for selective dispensing of a known or ascertainable mass of fluid it is capable of containing for introduction into the volume within said first enclosure thereby to displace a correlative mass of the vapor phase fluid the first enclosure is capable of containing, causing said correlative mass to be dispensed to said instrument; and a valve in communicating relationship with said first enclosure and positioned such that, when the first enclosure is interconnected with said instrument, the valve is interposed between the interconnected first enclosure and instrument, which valve is capable of selectively permitting flow to said instrument of said vapor phase fluid dispensed from the first enclosure upon being displaced by said introduction of fluid from the second enclosure.

In still another aspect, the invention is a method of dispensing to a detection instrument a known or ascertainable mass of a fluid in gas form comprising: in a first enclosure interconnected with said instrument and containing said fluid, maintaining conditions such that the fluid is present in part as a vapor phase and in part as a liquid phase in equilibrium with one another; in a second enclosure interconnected with said first enclosure and containing either the same or a different fluid in gas form as compared with the first enclosure, subjecting the fluid in the second enclosure to conditions sufficient to effect an expansion of the fluid in gas form, such that a known or ascertainable mass of said fluid in gas form is dispensed from the second enclosure and introduced into said first enclosure, thereby to displace a correlative mass of the vapor phase fluid in the first enclosure, causing said correlative mass to be dispensed to the instrument; and selectively permitting said correlative mass to flow through to the instrument.

Practice of the invention results in substantial advantages. The invention is useful for generating small quantifiable aliquots of a broad spectrum of vapors. This includes, without limitation, any material that is a liquid at the operating temperature of the apparatus. In addition, the invention can be used to generate vapors from various materials that are low volatility solids. Practice of the invention is furthermore very economical in terms of space requirements (for example, the apparatus of the invention is very compact, making it suitable for incorporation in the chemical instrumentation for which calibration is sought). Moreover, the invention allows the simple generation of small volumes of vapor suitable for use with high sensitivity instruments (for instance, microliter volumes). By dispensing small amounts of vapor, the lifetime of the reservoir from which the vapor comes is extended, thereby minimizing maintenance. Further, the volume of vapor dispensed is more easily controlled, such as by selecting the temperature of equipment (for example, a pump system or other suitable component) inducing flow of the vapor amount. Thus, with the invention, one can deliver a precise vapor amount in a short period of time, on the order of seconds.

These and other benefits conferred by the invention are described as well in the following discussion.

DESCRIPTION OF CERTAIN PREFERRED EMBODIMENTS

As indicated above, a central feature of the invention is provision of a known or ascertainable vapor mass suitable for use in verifying the proper operation of a chemical detection instrument. This is advantageously accomplished simply and repeatedly in accordance with the invention, by displacing a desired mass of fluid from a pump module (as discussed in more detail hereinafter), which mass of fluid has a proportionally related volume, such that said volume flows to an interconnected fluid reservoir where it displaces a like volume of fluid from said reservoir, said like volume of fluid in turn having a proportionally related mass that is known or ascertainable; the latter mass can then, for instance, be introduced into a detection instrument. It will be appreciated that, since such latter mass is related to the volume displaced from the reservoir and therefore the volume—and the mass—of the fluid displaced from the pump module, the mass of the fluid displaced from the reservoir is correlative with the mass displaced from the pump module. As used herein, the terms "correlative," "correlatively," etc., shall refer to the proportional (and calculable) relationship between the mass of fluid displaced from the reservoir and the mass of the fluid displaced from the pump module. Practice of the invention affords its practitioner a reliability of result, as well as a readiness and versatility of application, representing a significant advance in the art.

Chemical vapor detection instruments which can be calibrated or the like in accordance with the invention are used in a wide variety of applications and industries, including the chemical, government, medical, food and beverage, semiconductor, automotive, pharmaceutical and petroleum markets. More specifically, any of a wide variety of these instruments is suitable for practice of the invention; such instruments typically consist of a handheld or mountable apparatus capable of detecting the presence and/or concentration of a selected chemical vapor in an environment of interest. Some examples include surface acoustic wave, gas chromatograph, and electrochemical cell array detection instruments and technologies. This reflects the invention's versatility.

That versatility is also reflected by the variations indetection instrument design which the invention accommodates. For instance, many chemical vapor detection instruments have a pump to pull at least a substantial portion of a sample into the instrument for analysis. When the detection instrument responds very quickly, then the invention permits one to establish, at least semi-quantitatively, whether or not the instrument is responding properly to the vapor. Other detection instruments collect the entirety of a vapor sample and thus perform discrete measurements on the whole sample, such that a quantitative calibration of the instrument is feasible.

Figure 1:
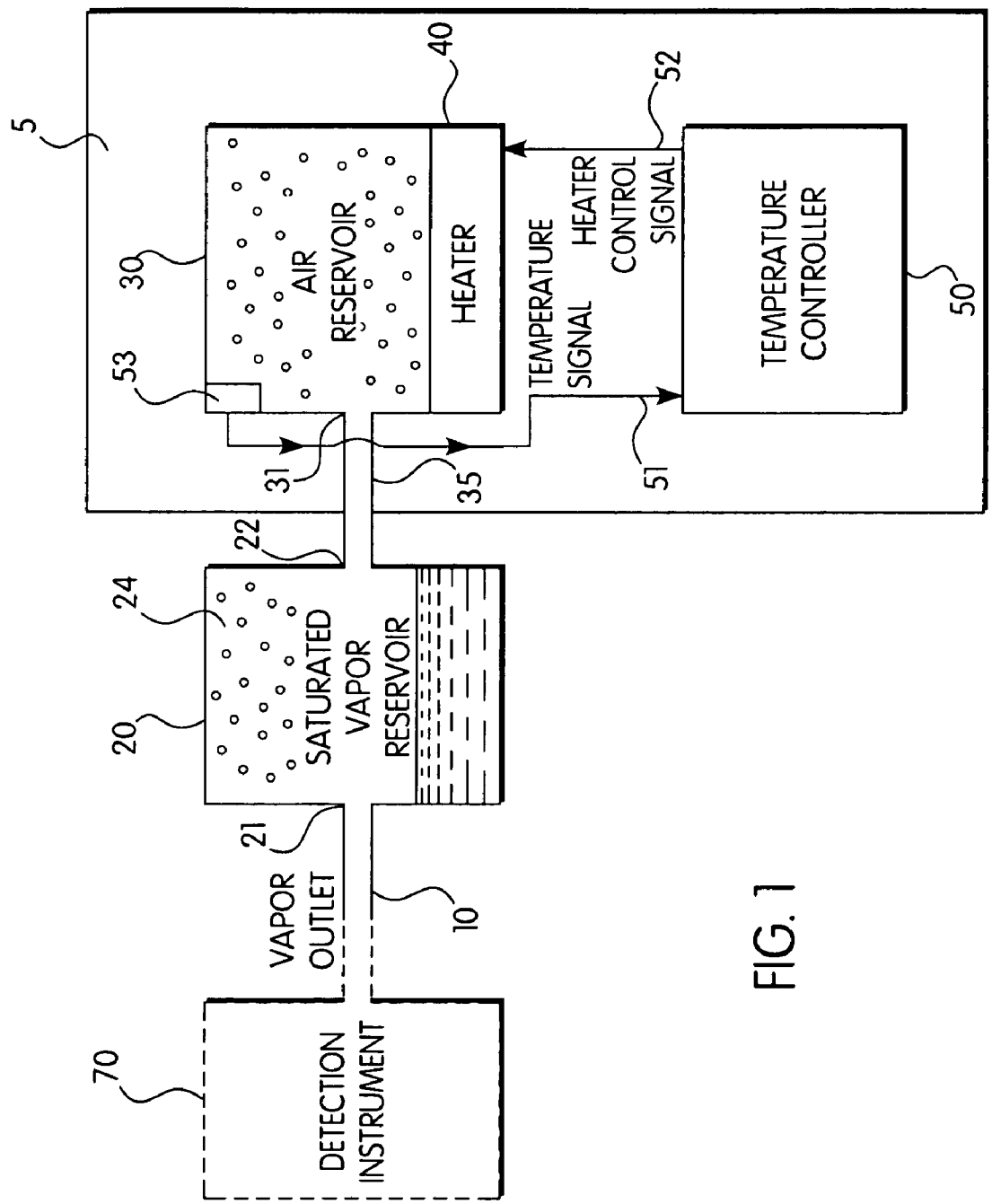
FIG. 1 is a schematic diagram showing an embodiment suitable for chemical vapor dispensing according to the present invention.

In accordance with FIG. 1, a preferred embodiment of the invention comprises a small first enclosure 20 containing a reservoir of the desired vapor to be dispensed, an outlet conduit 10 from the enclosure, and a pump module 5. Such pump module is a highly advantageous feature of preferred embodiments of the invention, and is formed by a combination of components that operate to achieve the result sought. Thus, in FIG. 1, the pump module 5 comprises (inter alia) a second enclosure 30 containing an air reservoir (connected to the first enclosure 20 and the vapor reservoir contained therein), a heating element 40 in thermal contact with the second enclosure, and a sensor 53 for ascertaining the amount of heat delivered to the air reservoir in the second enclosure. Prior to operation, the vapor reservoir is allowed to remain in a quiescent state long enough to allow the headspace material in the second enclosure to reach saturated equilibrium with the liquid in that enclosure. Generally, the time required to reestablish vapor reservoir equilibrium after a heating cycle is brief (e.g., several minutes), especially when small amounts of the reservoir (e.g., less than 1%) are dispensed.

More specifically, in the embodiment depicted in FIG. 1, there is a small pump module 5 to displace a precise mass of saturated vapor and cause it to be delivered to the instrument to be calibrated. The pump includes an air reservoir in enclosure 30 maintained at ambient pressure. The air reservoir in enclosure 30, via port 31, is in communication with conduit 35, which is also in communication with enclosure 20 and the reservoir of saturated vapor contained therein, via port 22. Enclosure 20 contains vapor and liquid in equilibrium, with the vapor occupying the headspace 24 within the enclosure. Ideally, the diameter and length of the conduit 35 will be chosen to minimize "dead" volume and to minimize diffusion when the pump module is off. Enclosure 20 and the vapor reservoir contained therein are similarly in communication with vapor outlet 10 via port 21 in enclosure 20. Vapor outlet 10 is in communication with detection instrument 70.

Heating element 40 is located abutting, and in thermal contact with, enclosure 30. When the user desires that a vapor sample be sent to vapor outlet 10, heating element 40 is energized to produce a predetermined temperature increase in the air reservoir in enclosure 30 that results in a predetermined amount of expansion of the air. A corresponding desired mass of air with a proportionally related volume overflows enclosure 30 into conduit 35, and travels into enclosure 20 and the vapor reservoir contained therein, thus displacing a like volume of vapor (having a correlative and thus known or ascertainable mass) from headspace 24 into the vapor outlet 10.

Vapor reservoir enclosure 20 and air reservoir enclosure 30 begin operation at the same temperature and pressure. When vapor is to be dispensed, heating element 40 is energized. The amount of heat provided by the heating element is regulated by temperature controller 50 (a processor) which sends signals to heating element 40 activating and deactivating such element through heater control signal line 52 and receives feedback from sensor 53 concerning the temperature of the contents of air reservoir enclosure 30 via temperature signal line 51.

As the air in the fixed volume of the air reservoir is warmed, the pressure inside the air reservoir enclosure increases, causing the enclosed air to expand and a desired mass/volume thereof to be transferred through conduit 35 and into vapor reservoir 20, thereby displacing a like volume of saturated headspace vapor into vapor outlet conduit 10 and on to detection instrument 70. Conduit 35, which runs between air reservoir enclosure 30 and vapor reservoir enclosure 20, also serves to cool the displaced air from the air reservoir conduit 30 so that it does not significantly disrupt the vapor equilibrium in headspace 24 through an infusion of a substantial amount of heat.

The desired amount of air is induced to exit air reservoir enclosure 30, into conduit 35 and via same into vapor reservoir enclosure 20, by causing the air of the reservoir to expand in corresponding amount via introduction of a predetermined amount of heat energy to the air reservoir. Heating element 40 is activated by temperature controller 50, and emits heat energy for an amount of time, such that the amount of heat energy necessary to effect the desired amount of expansion is transferred to the contents of air reservoir enclosure 30, and then the heating element is deactivated. The amount of heat introduced can be managed by setting the duration of the heating period, or by keying such duration to feedback from temperature signal line 51 concerning the temperature of the air in the air reservoir. At the point the heating cycle is concluded, expansion of the air in the air reservoir is arrested, the temperature of the air in the air reservoir decreases, and the internal pressure in air reservoir enclosure 30 drops, and in turn the pressure in vapor reservoir enclosure 20 also drops, causing ambient air to be drawn back into vapor output conduit 10. Thus, the system effectively "breathes out" when heat is applied and "breathes in" when the heat is removed.

Figure 2:
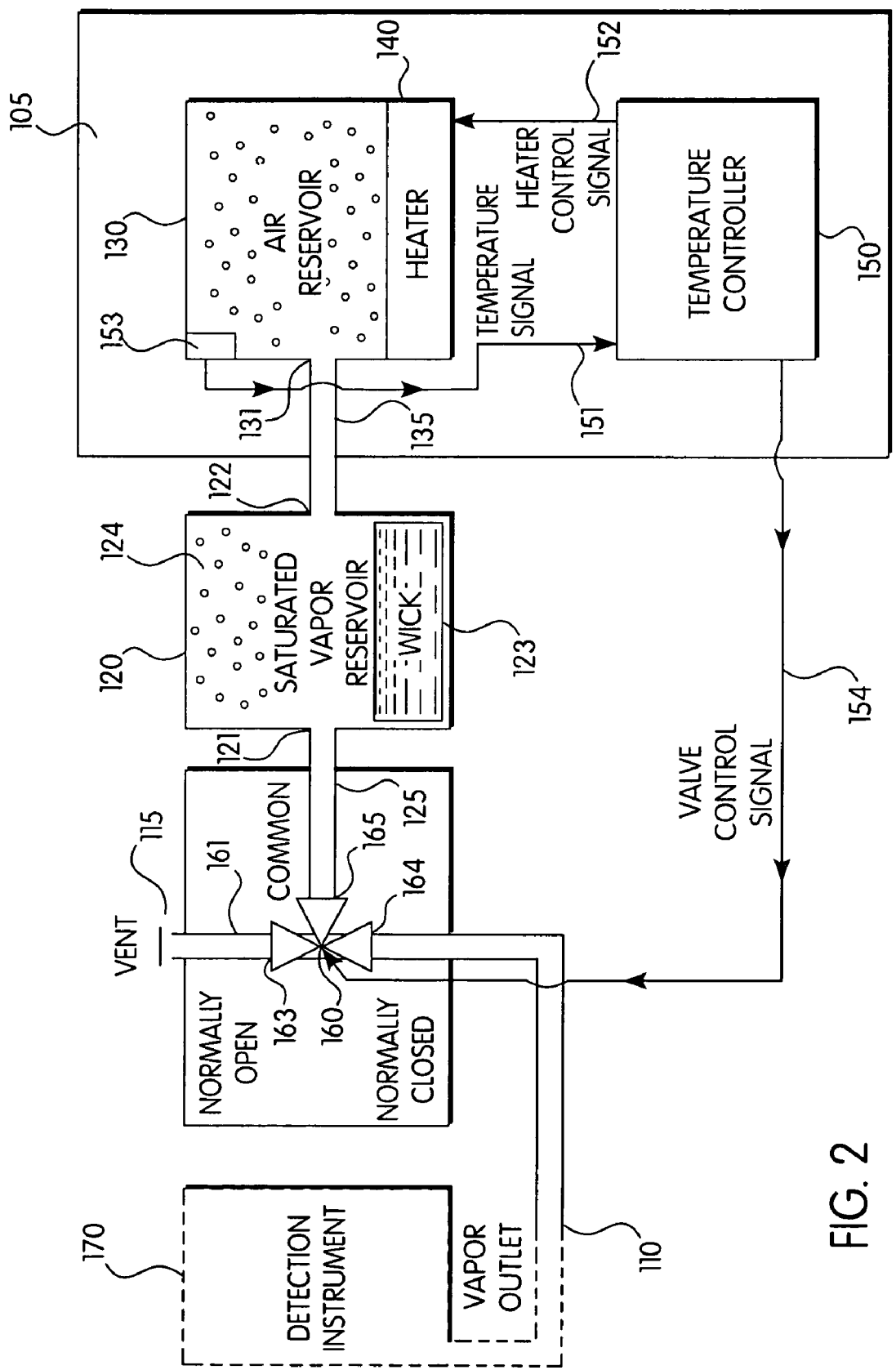
FIG. 2 is a schematic diagram showing another embodiment suitable for chemical vapor dispensing according to the present invention.

In another preferred embodiment, shown in FIG. 2, air reservoir conduit 130, heater 140, temperature controller 150, temperature signal line 151, heater control signal line 152, and sensor 153 cooperate to provide, in effect, pump module 105 which delivers a desired amount of air to a vapor reservoir for the purpose of causing same to furnish a known or ascertainable amount of vapor to an instrument of interest. Thus, there is an air reservoir enclosure 130, interconnected with a vapor reservoir enclosure 120, by conduit 135 running between them; air flows from the air reservoir to the vapor reservoir within enclosure 120. Vapor reservoir enclosure 120 is in turn interconnected via conduit 125 to port 165 of three-way valve 160, which, in turn, is interconnected with a vent 115 via conduit 161 and a vapor outlet conduit 110 (which outlet is in communication with the instrument to be calibrated). In the normal position of three-way valve 160, the connection through port 164 to vapor outlet conduit 110 is closed, and the vapor reservoir will be cut off from the outlet to the instrument. In this regard, valve 160 ensures that small ambient temperature variations in the apparatus will not result in vapor reservoir's "breathing-out" vapor through vapor outlet conduit 110 to detection instrument 170.

Furthermore, in its normal position, three-way valve 160 provides an unobstructed path from the vapor reservoir through port 163 in valve 160 to conduit 161, which leads to vent 115. Access to the ambient atmosphere results in pressure equalization between the vapor reservoir and the air reservoir, so that when the pump module 105 is activated, the volume produced by the air reservoir will be equal to the volume displaced from vapor reservoir. Additionally, since in its normal position three-way valve 160 closes off communication with vapor outlet conduit 110, the "breathe in" cycle of the pump bypasses conduit 110, thereby leaving the vapor occupying such path undisturbed and assuring higher precision of the vapor volume delivered in the subsequent cycle.

The preferred embodiment uses an electrically activated heater and an electrically controlled valve. Temperature control element 150 is a processor that governs the amount of heat delivered by activating and thereafter deactivating heating element 140 such that it either operates for a desired period of time or operates until the contents of air reservoir enclosure 130 reach the desired temperature as indicated to the control element by feedback from sensor 153 received via temperature signal line 151 and then shuts off when the desired end temperature has been reached. (Sensor 153 is preferably an electrical temperature sensing device, for example, a thermocouple or thermistor; however, the sensor can consist of any device capable of delivering a temperature feedback signal to the temperature control element 150.) Likewise, the action of valve 160 is controlled by a processor, which sends signals to the valve causing it to move between the positions discussed in the preceding paragraph. In the preferred embodiment, the temperature control element 150 electrically controls the operation of valve 160 by sending signals to the valve over valve control signal line 154. Effective results can be obtained if the operation of valve 160 is correlated with the application of heat to air reservoir enclosure 130.

In an advantageous variation, a wick is provided inside vapor reservoir enclosure 120 to store the liquid contents of the vapor reservoir enclosure. This eliminates the presence of neat liquid in the reservoir and the attendant problem that, when neat liquid is present, the proper orientation of the reservoir must be carefully maintained at all times or liquid might be allowed to flow into the outlet conduit with undesirable consequences. In contrast, the use of a wicking element eliminates the need to maintain a particular gravitational orientation of the device. Of course, even when the liquid phase is "held" by the wicking element it is nonetheless present as though it were in "neat" form for the-purpose of maintaining equilibrium with the vapor phase such that the latter is saturated. In accordance with the foregoing, wick 123 is shown in FIG. 2.

The delivery of a precise mass, and thus volume, of air (or other fluid) from the so-called pump module—and in turn the delivery of a like volume and correlative mass of fluid from the reservoir as aforesaid—can be effectuated in accordance with the ideal gas law, which is applicable to gases under ambient temperatures and pressures. Under the ideal gas law $$P*V=n*R*T$$

wherein P=gas pressure, V=gas volume, n=the number of moles of gas, R=the ideal gas constant, and T=absolute temperature. Alternatively, the equation can be rewritten $$V/T=n*R/P.$$

It is evident from this relationship that if variables P, n, and R are held constant, a directly proportional relationship will exist between the temperature of a gas and its volume, with the result that an increase in temperature will result in a directly proportional increase in volume. Assuming constant values of variables P, n, and R, this relationship can be simplified to:

$$V_1/T_1=V_2/T_2.$$

For instance, a "pump" cell volume of 1 cc at an ambient temperature of 298° K will deliver 0.02 cc of air volume (i.e., $\partial V=0.02$ cc) if it is heated to a temperature of 304° K (i.e., $\partial T=6$ degrees). If the headspace vapor concentration is known, then it is possible to calculate the mass of vapor delivered to the instrument being calibrated. For example, if the headspace vapor concentration is 5000 μg/L and the volume delivered is 0.00002 L (i.e., 0.02 cc) then the amount of mass delivered is 0.1 μg. The amount of vapor mass dispensed by this invention can be calculated using the following expression:

$$m=[(T_2-T_1)/T_1]*V_{pump}*C_{sat}$$

wherein m=the mass of vapor delivered (μg)
$T_2$=the final temperature of the pump (°K)
$T_1$=the initial temperature of the pump (°K)
$V_{pump}$=the volume of the pump (L)
$C_{sat.}$=the vapor headspace concentration (μg/L)

The absolute accuracy of the mass delivered from vapor reservoir 20 or 120 (as the case may be) depends on the absolute temperature and pressure of the vapor reservoir since these parameters determine the saturated headspace vapor concentration. For the highest accuracy, temperature controller 50 or 150 (again, as the case may be) comprises a microcomputer with the ability to ascertain the absolute temperature and pressure of the vapor reservoir. Using the temperature and pressure information in conjunction with known vapor pressure curves for the reservoir vapor, the microcomputer can calculate the corresponding final temperature of the air in the air reservoir 30 or 130 required for delivery of the precise vapor mass desired. While this extent of control is not always necessary (for example, where the reservoir temperature does not undergo wide variation or where only semi-quantitative vapor quantities are adequate), it is often advantageous to operate at a high level of accuracy.

The invention described herein is susceptible of many modifications and variations within its scope, and in particular extends to the use of any one or more of the singular and several features of the foregoing description and accompanying drawings and their equivalents.

What is claimed is:

1. A system for testing the operation of a detection instrument, comprising:
a first enclosure having at least two ports and containing fluid comprising a substance detectable in gas form by the instrument, said fluid being present in part as a vapor phase and in part as a liquid phase in equilibrium with one another, said first enclosure being interconnected with the instrument such that the fluid contained in the first enclosure can be dispensed to the instrument via at least one port of said first enclosure;
a second enclosure having at least one port and containing either the same or a different fluid in gas form as compared with the first enclosure, said second enclosure being adapted for selective dispensing of a known or ascertainable mass of fluid contained therein via at least one port thereof, and being interconnected with said first enclosure such that said mass can be introduced into the volume within said first enclosure through at least one port thereof, thereby to displace a correlative mass of the vapor phase fluid contained in the first enclosure causing said correlative mass to be dispensed to said instrument;
a valve in communicating relationship with said first enclosure and positioned such that, when the first enclosure is interconnected with said instrument, the valve is interposed between the interconnected first enclosure and instrument, which valve is capable of selectively permitting flow to said instrument of said vapor phase fluid dispensed from the first enclosure upon being displaced by said introduction of fluid from the second enclosure;
a heating element in thermal contact with the second enclosure such that heat energy from said element is imparted to the contents of said enclosure; and
a processor electrically connected to the heating element, which processor is capable of activating the heating element, and of deactivating the heating element a predetermined time after it activates said element.

2. The system as defined in claim 1, which further comprises a length conduit interconnected said second enclosure and said first enclosure, the dimensions and configuration of said length of conduit being such that dead volume and diffusion from or into either of the enclosures is reduced.

3. The system as defined in claim 1, which further comprises a sensor that is positioned so as to be in contact with the contents of the second enclosure and that is capable of ascertaining the temperature of said contents, said sensor being electrically connected to the processor such that the processor receives signals therefrom permitting the processor to recognize an increase in temperature of said contents and in response to attainment of a predetermined increment of temperature increase deactivates the heating element.

4. The system as defined in claim 1 wherein the processor is a microcomputer.

5. The system as defined in claim 1, wherein said valve is a three-way valve having one port communicating with a vent to the ambient atmosphere, one port communicating with the detection instrument, and one port communicating with the interior volume of the first enclosure, said valve being capable of alternating between its normal position in which the port communicating with the detection instrument is closed and another position in which the port communicating with the vent is closed.

6. The system as defined in claim 5, wherein the valve's movement between its normal position and said other position is electrically actuated.

7. The system as defined in claim 1, wherein the entire amount of vapor phase fluid dispersed from said first enclosure is analyzed by said instrument and a quantitative measurement thereof is performed.

8. An apparatus for dispensing a known or ascertainable mass of a fluid in gas form to a detection instrument, comprising:
   a first enclosure adapted for interconnection with the instrument and capable of containing said fluid when present in part as a vapor phase and in part as a liquid phase in equilibrium with one another;
   interconnected with the first enclosure, a second enclosure capable of containing either the same or a different fluid in gas form as compared with the first enclosure, said second enclosure being adapted for selective dispensing of a known or ascertainable mass of fluid it is capable of containing for introduction into the volume within said first enclosure thereby to displace a correlative mass of the vapor phase fluid the first enclosure is capable of containing, causing said correlative mass to be dispensed to said instrument;
   a valve in communicating relationship with said first enclosure and positioned such that, when the first enclosure is interconnected with said instrument, the valve is interposed between the interconnected first enclosure and instrument, which valve is capable of selectively permitting flow to said instrument of said vapor phase fluid dispensed from the first enclosure upon being displaced by said introduction of fluid from the second enclosure;
   a heating element in thermal contact with the second enclosure such that heat energy from said element can be imparted to the contents of said enclosure when the apparatus is connected to the detection instrument and the first and second enclosures contain said fluid or fluids; and
   a processor electrically connected to the heating element, which processor is capable of activating the heating element, and of deactivating the heating element a predetermined time after it activates said element.

9. The apparatus as defined in claim 8, which further comprises a length of conduit interconnecting said second enclosure and said first enclosure, the dimensions and configuration of said length of conduit being such that dead volume and diffusion from or into either of the enclosures is reduced when the apparatus is connected to the detection instrument and the reservoirs contain said fluid or fluids.

10. The apparatus as defined in claim 8, which further comprises a sensor that is positioned so as to be in contact with the fluid in the second enclosure and that is capable of ascertain the temperature of said fluid, said sensor being electrically connected to the processor such that the processor receives the signals therefrom permitting the processor to recognize an increase in temperature of said fluid and in response to attainment of a predetermined increment of temperature increase deactivate the heating element.

11. The apparatus as defined in claim 8, wherein the processor is a microcomputer.

12. The apparatus as defined in claim 8, wherein said valve is a three-way valve having one port adapted for communicating with a vent to the ambient atmosphere, one port adapted for communicating with the detection instrument, and one port communicating with the first enclosure, said valve being capable of alternating between its normal position in which the port adapted for communicating with the detection instrument is closed and another position in which the port adapted for communicating with the vent is closed.

13. The apparatus as defined in claim 12, wherein the valve's movement between its normal position and said other position is electrically actuated.

14. The apparatus as defined in claim 8, wherein the entire amount of vapor phase fluid dispensed from said first enclosure is analyzed by said instrument and a quantitative measurement thereof is performed.

15. A method of dispensing to a detection instrument a known or ascertainable mass of a fluid in gas form comprising:
   maintaining conditions in a first enclosure, interconnected with said instrument and containing said fluid such that the fluid is present in part as a vapor phase and in part as a liquid phase in equilibrium with one another;
   imparting heat energy to a fluid in gas form in a second enclosure interconnected with said first enclosure, which fluid in gas form in said second enclosure is either the same as or different from the fluid in gas form in the first enclosure said heat energy being imparted by means of a heating element in thermal contact with the second enclosure and in an amount sufficient to effect an expansion of the fluid in gas form in said second enclosure, via activating the heating element by means of a processor electrically connected to said heating element and deactivating the heating element by means of said processor a predetermined time after activating it, such that a known or ascertainable mass of said fluid in gas form is dispensed from the second enclosure and introduced into the volume within said first enclosure, thereby to displace a correlative mass of the vapor phase fluid in the first enclosure, causing said correlative mass to be dispensed to the instrument and
   selectively permitting said correlative mass to flow through to the instrument.

16. The method as defined in claim 15, wherein said second enclosure and said first enclosure are interconnected by a length of conduit, the dimensions and configuration of said length of conduit being such that dead volume and diffusion from or into either of the enclosures is reduced.

17. The method as defined in claim 15, which further comprises ascertaining the temperature of the fluid contained in said second enclosure, by means of a sensor that is positioned so as to be in contact with said fluid, said sensor being electrically connected to the processor such that the processor receives signals therefrom permitting the processor to recognized an increase in temperature of said contents, and deactivating the heating element in response to attainment of a predetermined increment of temperature increase.

18. The method as defined in claim 15, wherein the processor is a microcomputer.

19. The method as defined in claim 15, wherein said valve is a three-way valve having one port communicating with a vent to the ambient atmosphere, one port communicating with the measurement instrument, and one port communicating with the interior volume of the first enclosure, said valve alternating between its normal position in which the port communicating with the measurement instrument is closed and another position in which the port communicating with the vent is closed.

20. The method as defined in claim 19, which further comprises electrically actuating the valve's movement between its normal position and said other position.

21. The method as defined in claim 15, which further comprises analyzing the entire amount of vapor phase fluid dispersed from said first enclosure in order to perform a quantitative measurement thereof.

* * * * *